(12) United States Patent
Jimenez et al.

(10) Patent No.: US 12,097,126 B2
(45) Date of Patent: Sep. 24, 2024

(54) EXPANDABLE INTERVERTEBRAL CAGE

(71) Applicant: Ex Technology, LLC, Seattle, WA (US)

(72) Inventors: Omar F. Jimenez, Seattle, WA (US); Yefim I. Safris, Golden Valley, MN (US)

(73) Assignee: Ex Technology, LLC, Seattle, WA (US)

( * ) Notice: Subject to any disclaimer, the term of this patent is extended or adjusted under 35 U.S.C. 154(b) by 0 days.

(21) Appl. No.: 17/954,496

(22) Filed: Sep. 28, 2022

(65) Prior Publication Data

US 2023/0104776 A1 Apr. 6, 2023

Related U.S. Application Data

(60) Provisional application No. 63/249,797, filed on Sep. 29, 2021.

(51) Int. Cl.
*A61F 2/44* (2006.01)
*A61F 2/30* (2006.01)

(52) U.S. Cl.
CPC .... *A61F 2/447* (2013.01); *A61F 2002/30507* (2013.01); *A61F 2002/30579* (2013.01); *A61F 2002/30904* (2013.01)

(58) Field of Classification Search
CPC ...... A61F 2/4455; A61F 2/446; A61F 2/4465; A61F 2/447; A61F 2002/30471;
(Continued)

(56) References Cited

U.S. PATENT DOCUMENTS 283,218 A  8/1883  Rycke
703,251 A  9/1902  Haire
(Continued)

FOREIGN PATENT DOCUMENTS

EP  1342456 A1  9/2003
EP  1552797 A2  7/2005
(Continued)

OTHER PUBLICATIONS

Printout from Video for OmniLIF Anterior Insertion Approach from Lumber Jax; https://seelio.com/w/fgf/omnilif-the-new-standard-in-spinal-deformity-correction-and-fusion?student=lumbarjax; dated Nov. 27, 2014, 7 pages.
(Continued)

*Primary Examiner* — Jan Christopher L Merene
(74) *Attorney, Agent, or Firm* — Merchant & Gould P.C.

(57) ABSTRACT

An expandable intervertebral cage device includes a first base plate and a second base plate, a distal block with an internal passage that mechanically couples to each base plate, and a proximal block comprising internal threading. The device has exactly two arm assemblies with one on each side. Each arm assembly comprises a first arm mechanically coupled to the first base plate and a second arm mechanically coupled to the second base plate. A screw is arranged partially within the internal threading of the proximal block and passes through the internal passage of the distal block, such that rotation of the screw relative to the distal block causes a change in distance between the distal block and the proximal block, and a corresponding change in the spacing and lordosis of the device.

20 Claims, 8 Drawing Sheets

(58) Field of Classification Search
CPC .. A61F 2002/30538; A61F 2002/30507; A61F 2002/30545; A61F 2002/30556; A61F 2002/30553
See application file for complete search history.

(56) References Cited

U.S. PATENT DOCUMENTS

| | | |
|---|---|---|
| 811,344 A | 1/1906 | Wands |
| 1,388,836 A | 8/1921 | Ripsch et al. |
| 1,500,859 A | 7/1924 | Wright |
| 1,547,946 A | 7/1925 | Myers |
| 2,106,088 A | 1/1938 | De Tar |
| 2,231,221 A | 2/1941 | Rector |
| 2,453,656 A | 11/1948 | Bullard, III |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boerner |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell et al. |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,109 A | 10/1984 | Kobelt |
| 4,516,303 A | 5/1985 | Kloster |
| 4,528,864 A | 7/1985 | Craig |
| 4,559,717 A | 12/1985 | Scire et al. |
| 4,630,495 A | 12/1986 | Smith |
| 4,691,586 A | 9/1987 | van Leijenhorst et al. |
| 4,694,703 A | 9/1987 | Routson |
| 4,869,552 A | 9/1989 | Tolleson et al. |
| 5,133,108 A | 7/1992 | Esnault |
| 5,172,442 A | 12/1992 | Bartley et al. |
| 5,181,371 A | 1/1993 | Deworth |
| 5,196,857 A | 3/1993 | Chiappetta et al. |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett et al. |
| 5,439,377 A | 8/1995 | Milanovich |
| 5,445,471 A | 8/1995 | Wexler et al. |
| 5,554,191 A | 9/1996 | Lahille et al. |
| 5,645,599 A | 7/1997 | Samani |
| 5,653,763 A | 8/1997 | Errico et al. |
| 5,664,457 A | 9/1997 | Nejati |
| 5,904,479 A | 5/1999 | Staples |
| 5,960,670 A | 10/1999 | Iverson et al. |
| 5,980,252 A | 11/1999 | Samchukov et al. |
| 5,988,006 A | 11/1999 | Fleytman |
| 6,039,761 A | 3/2000 | Li et al. |
| 6,045,579 A | 4/2000 | Hochshuler et al. |
| 6,056,491 A | 5/2000 | Hsu |
| 6,080,193 A | 6/2000 | Hochshuler et al. |
| 6,136,031 A | 10/2000 | Middleton |
| 6,175,989 B1 | 1/2001 | Carpentar et al. |
| 6,190,414 B1 | 2/2001 | Young et al. |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,454,807 B1 | 9/2002 | Jackson |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley et al. |
| 6,802,229 B1 | 10/2004 | Lambert |
| 6,808,537 B2 | 10/2004 | Michelson |
| 6,863,673 B2 | 3/2005 | Gerbec et al. |
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici et al. |
| 7,070,598 B2 | 7/2006 | Lim et al. |
| 7,087,055 B2 | 8/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith et al. |
| 7,316,381 B2 | 1/2008 | Hacker et al. |
| 7,410,201 B1 | 8/2008 | Wilson et al. |
| 7,425,103 B2 | 9/2008 | Perez-Sanchez |
| 7,431,735 B2 | 10/2008 | Liu et al. |
| 7,435,032 B1 | 10/2008 | Murphey et al. |
| 7,547,325 B2 | 6/2009 | Biedermann et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Trieu |
| 7,708,779 B2 | 5/2010 | Edie et al. |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,901,409 B2 | 3/2011 | Canaveral et al. |
| 7,947,078 B2 | 5/2011 | Siegal |
| 7,985,256 B2 | 7/2011 | Grotz et al. |
| 8,057,549 B2 | 11/2011 | Butterman et al. |
| 8,070,813 B2 | 12/2011 | Grotz et al. |
| 8,088,163 B1 | 1/2012 | Kleiner |
| 8,192,485 B2 | 6/2012 | Simpson et al. |
| 8,303,663 B2 | 11/2012 | Jimenez et al. |
| 8,496,706 B2 | 7/2013 | Ragab et al. |
| 8,523,944 B2 | 9/2013 | Jimenez et al. |
| 8,540,452 B2 | 9/2013 | Jimenez et al. |
| 8,628,577 B1 | 1/2014 | Jimenez |
| 8,636,746 B2 | 1/2014 | Jimenez et al. |
| 8,771,360 B2 | 7/2014 | Jimenez et al. |
| 8,795,366 B2 | 8/2014 | Varela |
| 8,894,712 B2 | 11/2014 | Varela |
| 8,906,100 B2 | 12/2014 | Jimenez |
| 8,932,302 B2 | 1/2015 | Jimenez et al. |
| 8,940,049 B1 | 1/2015 | Jimenez et al. |
| 9,358,125 B2 | 6/2016 | Jimenez et al. |
| 9,381,092 B2 | 7/2016 | Jimenez et al. |
| 9,445,917 B2 | 9/2016 | Jimenez et al. |
| 9,474,626 B2 | 10/2016 | Jimenez |
| 9,486,328 B2 | 11/2016 | Jimenez |
| 9,498,270 B2 | 11/2016 | Jimenez |
| 9,668,879 B2 | 6/2017 | Jimenez et al. |
| 9,801,734 B1 | 10/2017 | Stein et al. |
| 9,820,865 B2 | 11/2017 | Sharabani et al. |
| 9,867,717 B2 | 1/2018 | Jimenez |
| 10,052,214 B2 | 8/2018 | Jimenez et al. |
| 10,060,469 B2 | 8/2018 | Jimenez et al. |
| 10,117,757 B2 | 11/2018 | Jimenez et al. |
| 10,363,142 B2 | 7/2019 | McClintock et al. |
| 10,369,008 B2 | 8/2019 | Jimenez et al. |
| 2002/0128716 A1 | 9/2002 | Cohen et al. |
| 2002/0138146 A1 | 9/2002 | Jackson |
| 2003/0077110 A1 | 4/2003 | Knowles |
| 2003/0233145 A1 | 12/2003 | Landry et al. |
| 2004/0049271 A1 | 3/2004 | Biedermann et al. |
| 2004/0111157 A1 | 6/2004 | Ralph et al. |
| 2004/0153156 A1 | 8/2004 | Cohen et al. |
| 2004/0193158 A1 | 9/2004 | Lim |
| 2004/0225364 A1 | 11/2004 | Richelsoph et al. |
| 2005/0000228 A1 | 1/2005 | De Sousa et al. |
| 2005/0033431 A1 | 2/2005 | Gordon et al. |

(56) References Cited

U.S. PATENT DOCUMENTS

| | | |
|---|---|---|
| 2005/0095384 A1 | 5/2005 | Wittmeyer, Jr. |
| 2005/0113921 A1 | 5/2005 | An et al. |
| 2005/0113924 A1 | 5/2005 | Buttermann |
| 2005/0175406 A1 | 8/2005 | Perez-sanchez |
| 2005/0182416 A1 | 8/2005 | Lim et al. |
| 2005/0261769 A1 | 11/2005 | Moskowitz et al. |
| 2006/0004447 A1 | 1/2006 | Mastrorio et al. |
| 2006/0004455 A1 | 1/2006 | Leonard et al. |
| 2006/0025862 A1 | 2/2006 | Villiers et al. |
| 2006/0058878 A1 | 3/2006 | Michelson |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0253201 A1 | 11/2006 | McLuen |
| 2006/0293752 A1 | 12/2006 | Moumene et al. |
| 2007/0032791 A1 | 2/2007 | Greenhalgh et al. |
| 2007/0049943 A1 | 3/2007 | Moskowitz et al. |
| 2007/0083267 A1 | 4/2007 | Miz et al. |
| 2007/0093901 A1 | 4/2007 | Grotz et al. |
| 2007/0129730 A1 | 6/2007 | Woods et al. |
| 2007/0173826 A1 | 7/2007 | Canaveral |
| 2007/0185577 A1 | 8/2007 | Malek |
| 2007/0191954 A1 | 8/2007 | Hansell et al. |
| 2007/0191958 A1 | 8/2007 | Abdou |
| 2007/0198089 A1 | 8/2007 | Moskowitz et al. |
| 2007/0219634 A1 | 9/2007 | Greenhalgh et al. |
| 2007/0222100 A1 | 9/2007 | Husted et al. |
| 2007/0250171 A1 | 10/2007 | Bonin, Jr. |
| 2007/0255415 A1 | 11/2007 | Edie et al. |
| 2007/0282449 A1 | 12/2007 | de Villiers et al. |
| 2007/0288092 A1 | 12/2007 | Bambakidis |
| 2007/0293329 A1 | 12/2007 | Glimpel et al. |
| 2007/0293948 A1 | 12/2007 | Bagga et al. |
| 2008/0026903 A1 | 1/2008 | Flugrad et al. |
| 2008/0077246 A1 | 3/2008 | Fehling et al. |
| 2008/0091211 A1 | 4/2008 | Gately |
| 2008/0100179 A1 | 5/2008 | Ruggeri et al. |
| 2008/0103601 A1 | 5/2008 | Biro et al. |
| 2008/0114367 A1 | 5/2008 | Meyer |
| 2008/0140207 A1 | 6/2008 | Olmos |
| 2008/0147194 A1 | 6/2008 | Grotz et al. |
| 2008/0154266 A1 | 6/2008 | Protopsaltis et al. |
| 2008/0161920 A1 | 7/2008 | Melkent |
| 2008/0161931 A1 | 7/2008 | Perez-Cruet et al. |
| 2008/0168855 A1 | 7/2008 | Giefer et al. |
| 2008/0183204 A1 | 7/2008 | Greenhalgh et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu et al. |
| 2008/0281423 A1 | 11/2008 | Sheffer et al. |
| 2008/0292392 A1 | 11/2008 | Voellmer |
| 2008/0319487 A1 | 12/2008 | Fielding et al. |
| 2009/0012564 A1 | 1/2009 | Chirico et al. |
| 2009/0076614 A1 | 3/2009 | Arramon |
| 2009/0099568 A1 | 4/2009 | Lowry et al. |
| 2009/0164017 A1 | 6/2009 | Sommerich et al. |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0259316 A1 | 10/2009 | Ginn et al. |
| 2009/0299478 A1 | 12/2009 | Carls et al. |
| 2009/0306672 A1 | 12/2009 | Reindel et al. |
| 2010/0004688 A1 | 1/2010 | Maas et al. |
| 2010/0076557 A1 | 3/2010 | Miller |
| 2010/0082109 A1 | 4/2010 | Greenhalgh et al. |
| 2010/0094305 A1 | 4/2010 | Chang et al. |
| 2010/0161062 A1 | 6/2010 | Foley et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez et al. |
| 2011/0015638 A1 | 1/2011 | Pischl et al. |
| 2011/0054616 A1 | 3/2011 | Kamran et al. |
| 2011/0093075 A1 | 4/2011 | Duplessis et al. |
| 2011/0112644 A1 | 5/2011 | Zilberstein et al. |
| 2011/0138948 A1 | 6/2011 | Jimenez et al. |
| 2011/0160861 A1 | 6/2011 | Jimenez et al. |
| 2011/0172774 A1 | 7/2011 | Varela |
| 2011/0270398 A1 | 11/2011 | Grotz et al. |
| 2012/0010653 A1 | 1/2012 | Seifert et al. |
| 2012/0029636 A1 | 2/2012 | Ragab et al. |
| 2012/0116518 A1 | 5/2012 | Grotz et al. |
| 2012/0158071 A1 | 6/2012 | Jimenez et al. |
| 2012/0185049 A1 | 7/2012 | Varela |
| 2012/0226357 A1 | 9/2012 | Varela |
| 2012/0271419 A1 | 10/2012 | Marik |
| 2012/0290094 A1 | 11/2012 | Lim et al. |
| 2012/0303124 A1 | 11/2012 | McLuen et al. |
| 2012/0323329 A1 | 12/2012 | Jimenez et al. |
| 2013/0053966 A1 | 2/2013 | Jimenez et al. |
| 2013/0088714 A1 | 4/2013 | Terada et al. |
| 2013/0144388 A1 | 6/2013 | Emery et al. |
| 2013/0158664 A1 | 6/2013 | Palmatier et al. |
| 2013/0197642 A1 | 8/2013 | Ernst |
| 2013/0317615 A1 | 11/2013 | Jimenez et al. |
| 2014/0012383 A1 | 1/2014 | Triplett et al. |
| 2014/0018924 A1 | 1/2014 | McManus et al. |
| 2014/0039622 A1 | 2/2014 | Glerum et al. |
| 2014/0140757 A1 | 5/2014 | Jimenez et al. |
| 2014/0156007 A1 | 6/2014 | Pabst et al. |
| 2014/0194991 A1 | 7/2014 | Jimenez |
| 2014/0236296 A1 | 8/2014 | Wagner et al. |
| 2014/0249629 A1 | 9/2014 | Moskowitz et al. |
| 2014/0343608 A1 | 11/2014 | Whiton et al. |
| 2015/0018951 A1 | 1/2015 | Leobl |
| 2015/0088258 A1 | 3/2015 | Jimenez et al. |
| 2015/0100128 A1 | 4/2015 | Glerum et al. |
| 2015/0148908 A1 | 5/2015 | Marino et al. |
| 2015/0272743 A1* | 10/2015 | Jimenez ............ A61F 2/447 623/17.16 |
| 2015/0272745 A1 | 10/2015 | Jimenez et al. |
| 2015/0272746 A1 | 10/2015 | Jimenez et al. |
| 2015/0351925 A1 | 12/2015 | Emerick et al. |
| 2016/0166369 A1 | 6/2016 | McClintock et al. |
| 2016/0262907 A1 | 9/2016 | Jimenez |
| 2016/0356368 A1 | 12/2016 | Jimenez et al. |
| 2016/0377113 A1 | 12/2016 | Jimenez et al. |
| 2017/0105844 A1* | 4/2017 | Kuyler ............... A61F 2/4611 |
| 2017/0216045 A1* | 8/2017 | Dewey ............... A61F 2/4611 |
| 2017/0319352 A1* | 11/2017 | Dewey ............... A61F 2/447 |
| 2017/0333198 A1* | 11/2017 | Robinson ........... A61F 2/4455 |
| 2019/0021868 A1* | 1/2019 | Ludwig .............. A61F 2/447 |
| 2019/0151111 A1* | 5/2019 | Dewey ............... A61F 2/4425 |
| 2021/0030561 A1* | 2/2021 | Gleason ............. A61F 2/4611 |

FOREIGN PATENT DOCUMENTS

| | | |
|---|---|---|
| EP | 1881209 A1 | 1/2008 |
| FR | 2372998 A1 | 12/1976 |
| JP | 05-81194 | 4/1993 |
| JP | 2004-301135 A | 10/2004 |
| JP | 2008208932 A | 9/2008 |
| WO | 2004026188 A2 | 4/2004 |
| WO | 2004109155 A1 | 12/2004 |
| WO | 2005081330 A2 | 9/2005 |
| WO | 2005096975 A2 | 10/2005 |
| WO | 2006094535 A1 | 9/2006 |
| WO | 2006116052 A2 | 11/2006 |
| WO | 2006125329 A1 | 11/2006 |
| WO | 2007002583 A2 | 1/2007 |
| WO | 2007009107 A2 | 1/2007 |
| WO | 2007028140 A2 | 3/2007 |
| WO | 2007076377 A2 | 7/2007 |
| WO | 2007111979 A2 | 10/2007 |
| WO | 2008137192 A1 | 11/2008 |
| WO | 2009018349 A2 | 2/2009 |
| WO | 2010078468 A2 | 7/2010 |
| WO | 2010078520 A2 | 7/2010 |
| WO | 2011011609 A2 | 1/2011 |

(56) References Cited

FOREIGN PATENT DOCUMENTS

| WO | 2011011626 A2 | 1/2011 |
|---|---|---|
| WO | 2014066890 A1 | 5/2014 |

OTHER PUBLICATIONS

Printout from Video for OmniLIF Features from Lumber Jax; https://seelio.com/w/fgf/omnilif-the-new-standard-in-spinal-deformity-correction-and-fusion?student+lumbarjax; dated Nov. 27, 2014, 11 pages.
Wenzel Spine, Inc., VariLift®-L Expandable Interbody Fusion Device: A proven solution for stand-alone fusion, Product Overview, 12 pages, 2010.
Peter A. Halverson, et al., Tension-based Multistable Compliant: Rolling-contact Elements, Department of Mechanical Engineering, Brigham Young University, Provo UT, USA 84602, 34 pages, 2007.
Just L. Herder, Force Directed Design of Laparoscopic Forceps, ASME Design Engineering Technical Conference, 8 pages, 1998.
Alexander H. Slocum, Fundamentals of Design, 2005.
W. Küsswetter, A Supplementary Instrumentation for Posterior Fusion of Spine in Scoliosis, Archives of Orthopedic Traumatic Surgery, 1980, 1 page.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.
Amelie Jeanneau, et al., A Compliant Rolling Contract Joint and its Application in a 3-DOF Planar Parallel Mechanism with Kinematic Analysis, ASME, Design Engineering Technical Conferences, 9 pages, 2004.
Hunter et al., Overview of Medical Devices, Department of Radiology, University of Arizona, Aug. 2001, pp. 89-140, vol. 30, No. 4, ISSN: 0363-0188.
Medtronic Sofamor Danek USA, Inc., CAPSTONE Instrument Set Technique, http://www.mtortho.com/public/capstone.pdf, © 2005, 25 pages.
Medtronic, CAPSTONE PEEK Spinal System Surgical Technique, http://www.mtortho.com/public/capstone_peek_st.pdf, © 2009, 36 pages.
Website printout from https://seelio.com/w/fgf/omnilif-the-new-standard-in-spinal-defprminty-correction-and-fusion?student=lumbarjax; dated Nov. 27, 2014, 5 pages.
Publication and File History for U.S. Appl. No. 12/407,608, filed Mar. 19, 2009, now U.S. Pat. No. 8,628,577, Inventors Jimenez et al.
Application and File History for U.S. Appl. No. 12/650,994, filed Dec. 31, 2009, now U.S. Pat. No. 8,523,944, Inventors Jimenez et al.
Application and File History for U.S. Appl. No. 12/651,266, filed Dec. 31, 2009 now U.S. Pat. No. 8,540,452, Inventors Jimenez et al.
Application and File History for U.S. Appl. No. 12/841,465, filed Jul. 22, 2010, now U.S. Pat. No. 8,303,663, Inventors Jimenez et al.
Application and File History for U.S. Appl. No. 12/841,869, filed Jul. 22, 2010, now U.S. Pat. No. 9,358,125, Inventors Jimenez et al.
Application and File History for U.S. Appl. No. 12/118,767, filed May 12, 2008, Inventor Jimenez.
Application and File History for U.S. Appl. No. 13/189,410, filed Jul. 22, 2011, now U.S. Pat. No. 8,636,746, Inventor Jimenez.
Application and File History for U.S. Appl. No. 13/661,534, filed Oct. 26, 2012, now U.S. Pat. No. 8,932,302, Inventor Jimenez.
Application and File History for U.S. Appl. No. 13/591,463, filed Aug. 22, 2012, now U.S. Pat. No. 8,771,360, Inventor Jimenez.
Application and File History for U.S. Appl. No. 13/891,356, filed May 10, 2013, now U.S. Pat. No. 8,906,100, Inventor Jimenez et al.
Application and File History for U.S. Appl. No. 14/024,764, filed Sep. 12, 2013, now U.S. Pat. No. 9,381,092, Inventor Jimenez et al.
Application and File History for U.S. Appl. No. 144/153,281, filed Jan. 13, 2014, now U.S. Pat. No. 9,867,717, Inventor Jimenez.
Application and File History for U.S. Appl. No. 14/563,660, filed Dec. 8, 2014, now U.S. Pat. No. 9,445,917, Inventor Jimenez et al.
Application and File History for U.S. Appl. No. 14/242,451, filed Apr. 1, 2014, now U.S. Pat. No. 8,940,049, Inventor Jimenez et al.
Application and File History for U.S. Appl. No. 14/318,196, filed Jun. 27, 2014, now U.S. Pat. No. 9,474,626. Inventor Jimenez et al.
Application and File History for U.S. Appl. No. 14/592,507, filed Jan. 8, 2015, now U.S. Pat. No. 9,498,270. Inventor Jimenez et al.
Application and File History for U.S. Appl. No. 14/585,544, filed Dec. 30, 2014, now U.S. Pat. No. 9,486,328. Inventor Jimenez et al.
Application and File History for U.S. Appl. No. 15/164,498, filed May 25, 2016, now U.S. Pat. No. 9,668,879. Inventors: Jimenez et al.
Application and File History for U.S. Appl. No. 15/174,454, filed Jun. 6, 2016, now U.S. Pat. No. 10,117,757. Inventors: Jimenez et al.
Application and File History for U.S. Appl. No. 15/332,066, filed Oct. 24, 2016, now U.S. Pat. No. 10,369,008. Inventors: Jimenez et al.
Application and File History for U.S. Appl. No. 15/198,557, filed Jun. 30, 2016, now U.S. Pat. No. 10,060,469. Inventors: Jimenez et al.
Application and File History for U.S. Appl. No. 15/591,214, filed May 10, 2017, now U.S. Pat. No. 10,052,214. Inventors: Jimenez et al.
Mirus IO Exandable Lumbar Interbody, 2021, 2 pages.
Mirus IO Exandable Lumbar Interbody, 2021, 28 pages.
Mirus IO Exandable Lumbar Interbody, 2020, 2 pages.
Mirus IO Expandable Lumbar Interbody wepage, https://www.mirusmed.com/solutions/spine/io-expandable-system/, accessed Apr. 23, 2023.
PCT/US2010/041941, filed Jul. 22, 2010, International Search Report and Written Opinion, dated Apr. 25, 2011.
PCT/US2010/042915, filed Jul. 22, 2010, Search Report and Written Opinion, dated Apr. 22, 2011.
PCT/US2009/069876, filed Dec. 30, 2009, International Search Report and Written Opinion dated Sep. 27, 2010, 10 pages.
PCT/US2009/069958, filed Dec. 31, 2009, International Search Report and Written Opinion dated Nov. 29, 2010, 7 pages.
PCT/US2015/055449, filed Oct. 14, 2015, International Search Report and Written Opinion dated Dec. 11, 2015, 9 pages.
PCT/US2015/032977, filed May 28, 2015, International Search Report and Written Opinion dated Sep. 21, 2015, 10 pages.
European Application No. EP 09837185, European Search Report dated May 14, 2013, 7 pages.
Japanese Application No. 2012-521784, JP Office Action dated Feb. 18, 2014, 8 pages.
PCT/US2013/067070, PCT Written Opinion/Search Report dated Feb. 27, 2014, 14 pages.
PCT/US2014/052913, PCT Written Opinion/Search Report dated Dec. 22, 2014, 10 pages.

* cited by examiner

EXPANDABLE INTERVERTEBRAL CAGE

RELATED APPLICATION

The present application claims the benefit of U.S. Provisional Application No. 63/249,797, filed Sep. 29, 2021, which is hereby incorporated herein in its entirety by reference.

TECHNICAL FIELD

The present disclosure relates generally to the distraction and fusion of vertebral bodies. More specifically, the present disclosure relates to devices and associated methods for distraction and fusion of vertebral bodies that remain stable when implanted and facilitate fusion following their use for distraction to aid in the correction of spinal deformity by reducing a collapsed disc and establishing sagittal alignment, lordosis, or kyphosis.

BACKGROUND

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone-to-bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

At least two devices have been commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root, allowing load sharing to enhance bone formation, and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted into the space within the intervertebral fusion device to promote the fusion of the vertebral bodies.

Intervertebral fusion and distraction can be performed through anterior, posterior, oblique, and lateral approaches. Each approach has its own anatomical challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

U.S. Pat. Nos. 7,070,598 and 7,087,055 to Lim et al. disclose minimally invasive devices for distracting the disc space. The devices include scissor-jack-like linkages that are used to distract a pair of endplates associated with adjacent vertebra from a first collapsed orientation to a second expanded orientation. A pull arm device is used to deliver and distract the device in the disc space. However, the device is primarily used for distraction and not subsequent vertebral fusion. The device would not work as a fusion device, because once the pull arm is disconnected from the device, the device will not be stable enough to maintain proper spacing of the vertebrae until fusion can occur. The endplates of the device are also solid and do not permit bone growth for successful fusion.

U.S. Patent Publication No. 2008/0114367 to Meyer discloses a device that uses a scissor-jack-like arrangement to distract a disc space. To solve the instability problem of the scissor-jack arrangement, a curable polymer is injected to fill the disc space and the distraction device is disabled from attempting to support the load. The curable polymer and disabling of the device are necessary because the device could not adequately support the distracted disc space. The base plates of the device have at least two or more degrees of freedom, collectively, in a distracted position and are therefore not stable under the loads encountered supporting the disc space. Absent injection of the polymer, and the support and control supplied by the implanting physician via the removable distraction tool, the base plates would collapse, which could cause severe damage to the vertebral bodies.

Accordingly, there is a need in the art for a device that can distract adjacent vertebral bodies in a minimally invasive manner while providing stable support for the disc space during fusion; particularly, a device that would allow for angular orientation of the base plates to be matched exactly to the unique alignment, or desired alignment, of a patient's spine.

SUMMARY

An expandable intervertebral cage device includes a first base plate and a second base plate, a distal block with an internal passage that mechanically couples to each base plate, and a proximal block comprising internal threading. The device has exactly two arm assemblies with one on each side. Each arm assembly comprises a first arm mechanically coupled to the first base plate and a second arm mechanically coupled to the second base plate. A screw is arranged partially within the internal threading of the proximal block and passes through the internal passage of the distal block, such that rotation of the screw relative to the distal block causes a change in distance between the distal block and the proximal block, and a corresponding change in the spacing and lordosis of the device.

In an embodiment, an expandable intervertebral cage device is adapted to be implanted into an intervertebral disc space in a patient's body. The device includes a first base plate having a first outer bearing surface configured to interface with a first vertebra of the intervertebral disc space, a second base plate having a second outer bearing surface configured to interface with a second vertebra of the intervertebral disc space, a proximal block comprising internal threading and an external ridge on each of a first side of the device and a second side of the device, the external ridges configured to move along corresponding tracks within the first base plate and the second base plate, a distal block comprising an internal passage, and two arm assemblies, wherein one arm assembly is on each of the first side of the device and the second side of the device. Each arm assembly includes a first arm mechanically coupled to the first base plate and the distal block and a second arm mechanically coupled to the second base plate and the distal block. The device further includes a screw extending between the internal threading of the proximal block and the internal passage of the distal block, such that rotation of the screw relative to the proximal block causes a change in distance between the distal block and the proximal block, and a corresponding change in the spacing and lordosis of the device due to an expansion or contraction of the arm assemblies as the external ridges on the proximal block are guided through the corresponding tracks within the first base plate and the second base plate.

In an embodiment, an expandable intervertebral cage device adapted to be implanted into an intervertebral disc space in a patient's body includes a first base plate having a first outer bearing surface configured to interface with a first vertebra of the intervertebral disc space, a second base plate having a second outer bearing surface configured to interface with a second vertebra of the intervertebral disc space, a proximal block comprising internal threading and an external arced surface on each of a first side of the device and a second side of the device, a distal block comprising an internal passage and one arm assembly on each of the first side of the device and the second side of the device. Each arm assembly can include a first arm mechanically coupled to the first base plate and the distal bloc and a second arm mechanically coupled to the second base plate and the distal block. A screw can extend between the internal threading of the proximal block and the internal passage of the distal block such that rotation of the screw relative to the proximal block causes a change in distance between the distal block and the proximal block and a corresponding movement of the first base plate and the second base plate along the external arced surfaces of the proximal block.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

In the following detailed description, numerous specific details are set forth in order to provide a thorough understanding of the disclosure. However, one skilled in the art will recognize that the embodiments may be practiced without these specific details. In other instances, well-known methods, procedures, and components have not been described in detail so as to not unnecessarily obscure aspects of the present disclosure. U.S. Pat. Nos. 8,628,577 and 9,486,328, invented by the inventor of the present application, disclose stable intervertebral body fusion and distraction devices. These patents are hereby incorporated herein by reference in their entirety other than the summary of the invention, claims and any express definitions set forth therein.

Figure 1A:
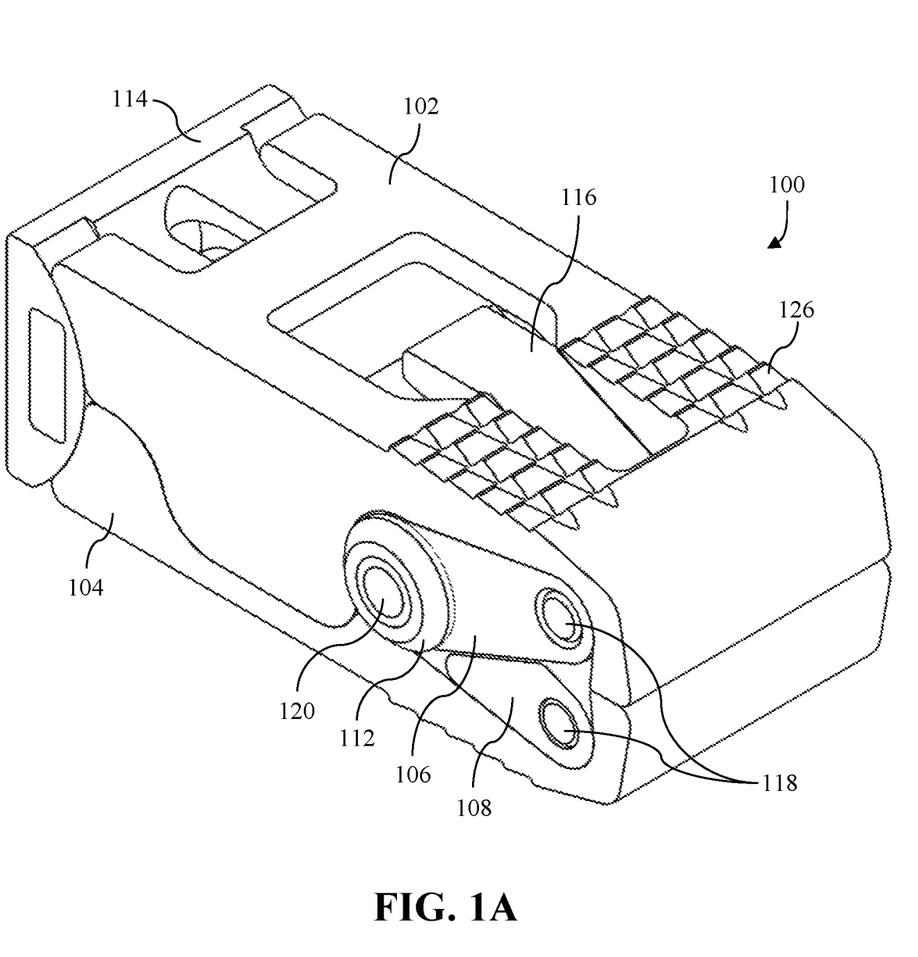
FIG. 1A is a perspective view of an expandable intervertebral cage device according to an aspect of the disclosure.
Figure 1B:
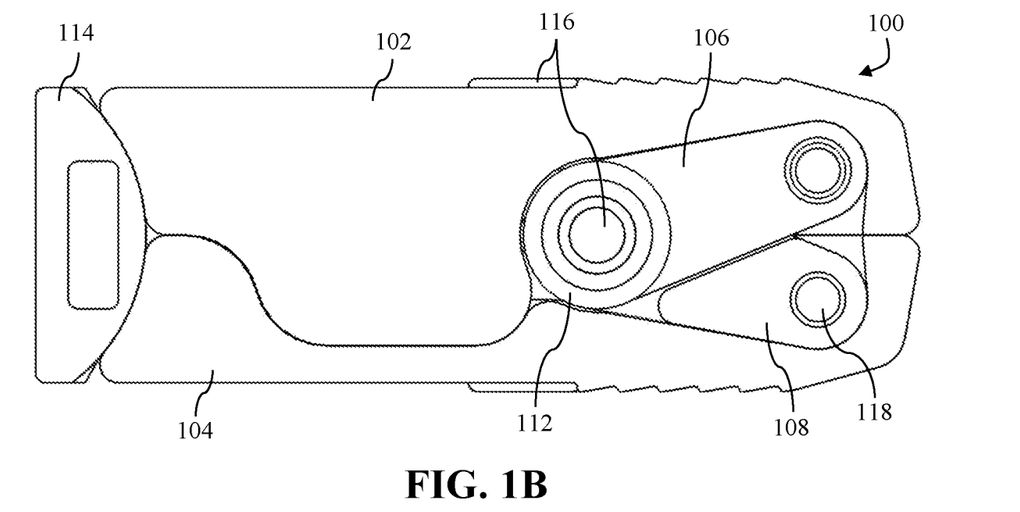
FIG. 1B is a side view of the expandable intervertebral cage device according to the embodiment of FIG. 1A.
Figure 1C:
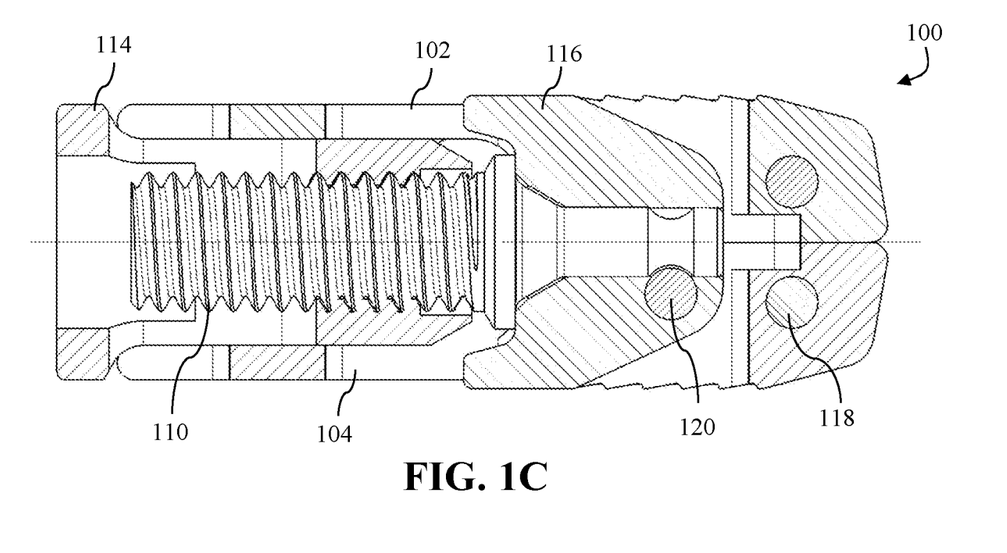
FIG. 1C is a cross-sectional view of the intervertebral cage device according to the embodiment of FIG. 1A.
Figure 2A:
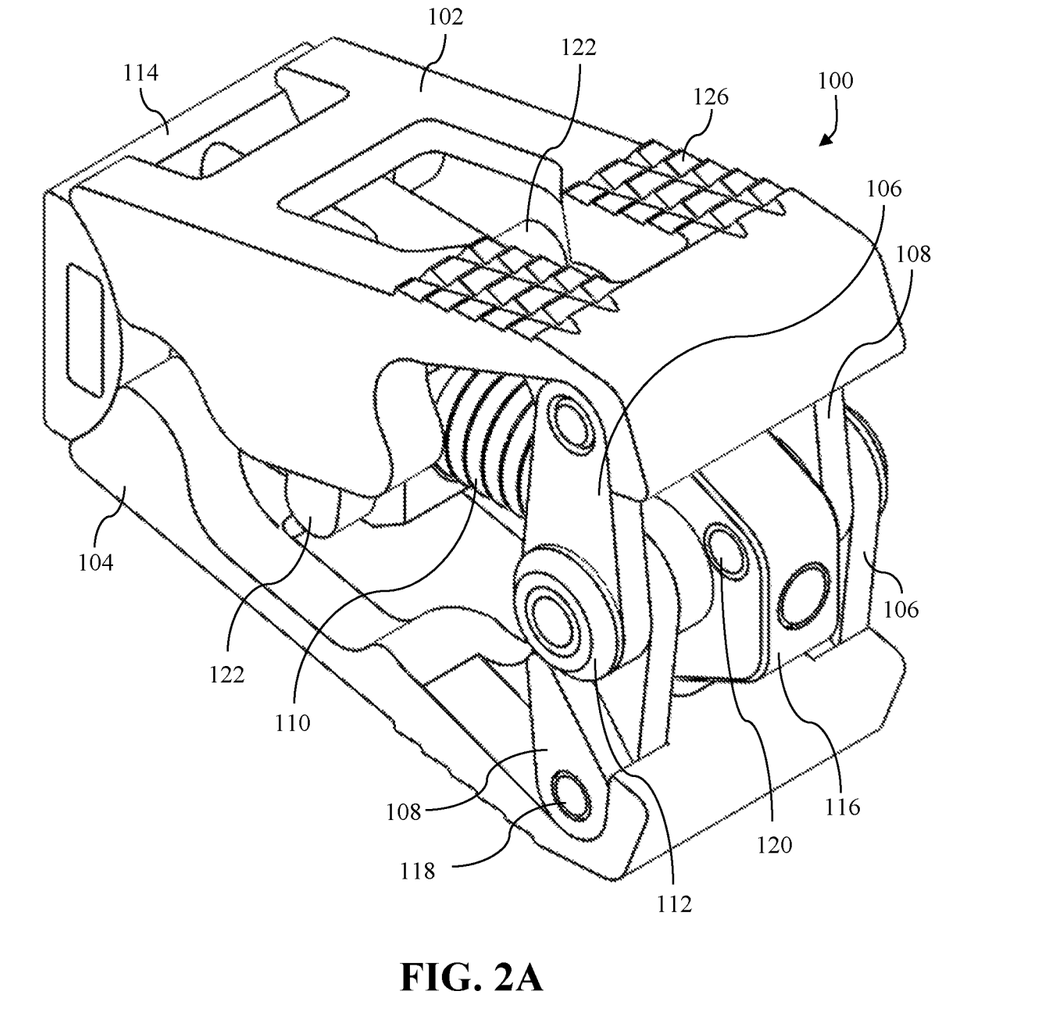
FIG. 2A is a perspective view of an expanded intervertebral cage device according to an embodiment.
Figure 2B:
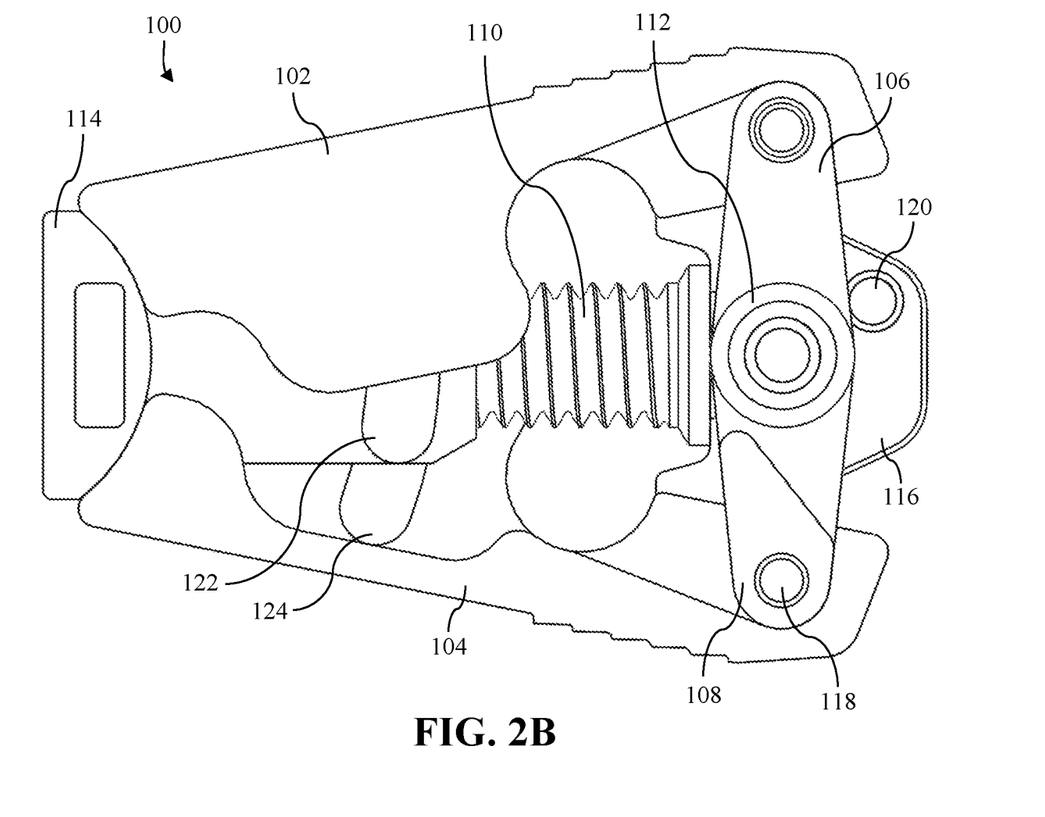
FIG. 2B is a side view of the expanded intervertebral cage device according to the embodiment of FIG. 2A.

FIG. 1A is a perspective view of an expandable intervertebral cage device 100. As shown in FIG. 1A, intervertebral cage device 100 is in a collapsed position. FIG. 1B is a side view of the intervertebral cage device 100 in the collapsed position, and FIG. 1C is a cross-sectional view of the intervertebral cage device 100. FIGS. 2A-2B are counterparts to FIGS. 1A-1C showing the same intervertebral cage device 100. However, in FIGS. 2A-2B, while the views of intervertebral cage device 100 are the same as their respective counterparts in FIGS. 1A-1C, device 100 is in a fully expanded configuration rather than the collapsed position. FIGS. 3-6 depict individual elements or parts of device 100 in isolation and in more detail.

Intervertebral cage device 100 includes first base plate 102 and second base plate 104. On each side (i.e., each edge perpendicular to both the base plates 102 and 104 and the proximal/distal axis), intervertebral cage device 100 includes first arm 106, second arm 108, screw 110, rings 112, first or proximal block 114, second or distal block 116, base plate pins 118, block pin 120, ridges 122, and tracks 124. The hidden side of intervertebral cage device 100, not visible in the perspective views herein, comprises many substantially similar structures to those described with reference to the numbered elements.

Intervertebral cage device 100 is a device that can be used to hold two structures, such as the vertebrae of a spine, in a fixed spatial relationship with respect to one another. Intervertebral cage device 100 can be expanded to hold structures in any fixed spatial relationship with a range of distances and angles with respect to one another. Intervertebral cage device 100 provides desirable spacing and lordosis and can be operated using a single screw, as described below, to achieve commonly used intervertebral spacing and lordosis levels. The use of a single screw device reduces the complexity and increases the mechanical strength of the device.

The degree of lordosis of an implant is defined by the acuate angle made by the intersection of the end places. In some embodiments, at full extension the intervertebral cage device 100 disclosed herein can exhibit greater than 24 degrees of lordosis. For example, in embodiments the implant can exhibit 25 degrees of lordosis or 26 degrees of lordosis, which is not possible in existing implants and can be provided thanks to the unique structural features of the implant disclosed herein, particularly the features that enable expansion at the proximal end of the device. In some embodiments, the implant 100 can have an insertion profile or height of 6 mm at the tapered distal end of the device and be expanded up to a maximum height of 20 mm. One way to provide such a profile while maintaining sufficient structural integrity to stably support the disc space is by forming the end plates from a carbon-metal composite.

As shown in more detail with respect to FIG. 1A, first base plate 102, which is substantially similar to second base plate 104, comprises textured surface 126. First plate 102 and second base plate 104 each comprise tracks 124 configured to receive ridges 122 of proximal block 114 as shown for second base plate 104 in FIG. 2B. The base plates 102, 104 are a portion of device 100 that comprises a bearing surface. As used throughout this disclosure, "bearing surface" refers to the outside surface of a base plate (e.g., 102, 104) that interfaces with the endplate of a vertebra, other bone, or other structures that are to be held in a fixed spatial relationship from one another. Textured surface 126 can comprise, for example, any texture that promotes bone growth to hold the base plates 102, 104, or which provides grip or traction when compressed against bone.

Figure 3:
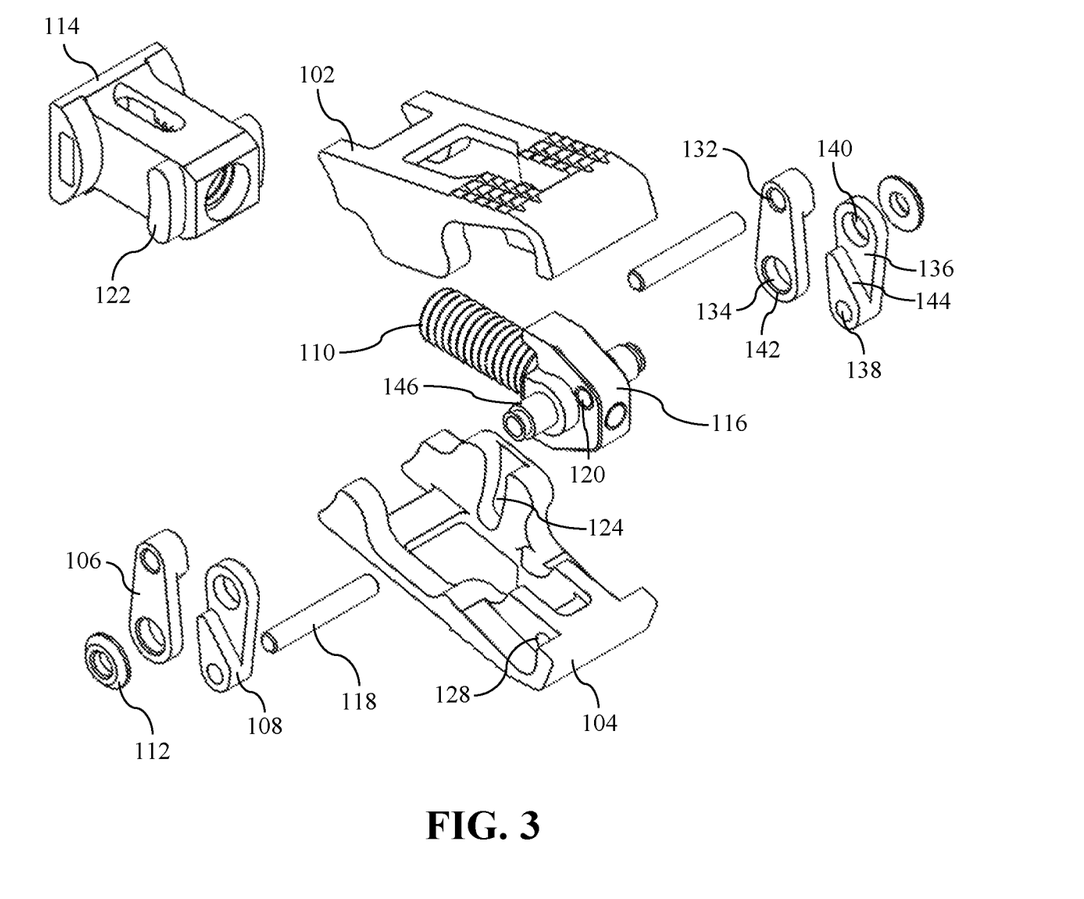
FIG. 3 is an exploded view of an expandable intervertebral cage device according to an embodiment.

As shown in FIG. 3, the base plates 102, 104 each further comprise socket 128 that are usable to receive base plate pins 118 to provide a mechanical connection between the base plates 102, 104 and a corresponding structure, such as first arms 106, as depicted in FIGS. 1A-11C.

As shown in FIGS. 1A-1C and 2A-2B, base plates 102 and 104 are arranged opposite from one another in device 100, and can be positioned within a range of distances and angles relative to one another, depending on the extent of the expansion of device 100. For example, as shown with respect to FIGS. 1A-1C, the device 100 is in a collapsed position, and base plates 102 and 104 are relatively close to one another, and arranged substantially parallel to one another. In the configuration shown with respect to FIGS. 2A-2B, the base plates 102 and 104 are relatively further away from one another on the distal end, and are angled relative to one another (this angle is sometimes referred to as lordosis). In embodiments, the extent of lordosis and/or distance between various parts of the base plates 102 and 104 can vary as the base plates ride along the curved surface of the proximal block. In some embodiments, base plates can define an angle of 23 degrees with respect to each other.

With continued reference to FIG. 3, the mechanism by which device 100 is expanded or collapsed is shown, and in particular first arms 106 and second arms 108. The arms 106, 108 are similar in function. First arms 106 comprise first body portion 130, first base connector 132, and first block connector 134. In embodiments, first block connector 134 further comprises groove 142. Second arms 108 comprise second body portion 136, second base connector 138, and second block connector 140. Body portions 130, 136 extend between base connectors 132, 138 and block connectors 134, 140 similarly for both first arms 106 and second arms 108. Second body portion 136 can further comprise arm protrusion 144. Arm protrusions 144 of second arms 108 are configured to abut first body portion 130 of first arms 106 when in a collapsed position, as shown in FIGS. 1A-1B, such that arms 106, 108 nest together in the collapsed configuration to enable the device to collapse to a smaller height and increase the difference in height between the collapsed configuration and the expanded configuration. The distance between base connectors 132, 138 and block connectors 134, 140 determines in part the extent to which the base plates 102, 104 of FIGS. 2A-2B can be distanced from one another, and the angle between them. Base connectors 132, 138 and block connectors 134, 140 can each be rotatably connected to an adjoining structure. So, for example, as shown with respect to FIGS. 1A-1C and 2A-2B, base connectors 132, 138 can be connected to first base plate 102 or second base plate 104 via a base plate pin 118. Likewise, block connectors 134, 140 can be connected to distal block 116 and secured using ring 112. The connections space the parts from one another, while allowing relative rotation between them.

In embodiments, rings 112 can support interconnection between the base plates 102, 104 and distal block 116. In particular, ring 112 holds block protrusions 146 (shown in more detail with respect to FIGS. 4-5) such that block protrusions 146 pass through block connectors 134 of first arms 106 and second arms 108. In operation, the effects of lateral forces (i.e., forces perpendicular to the proximal-distal directions previously described) are mitigated by ring 112. Ring 112 can prevent some types of relative lateral movement between first base plate 102, second base plate 104, first arms 106, and second arms 108 with respect to distal block 116. Ring 112 does this by snapping into grooves 142 of first arms 106.

Figure 4:
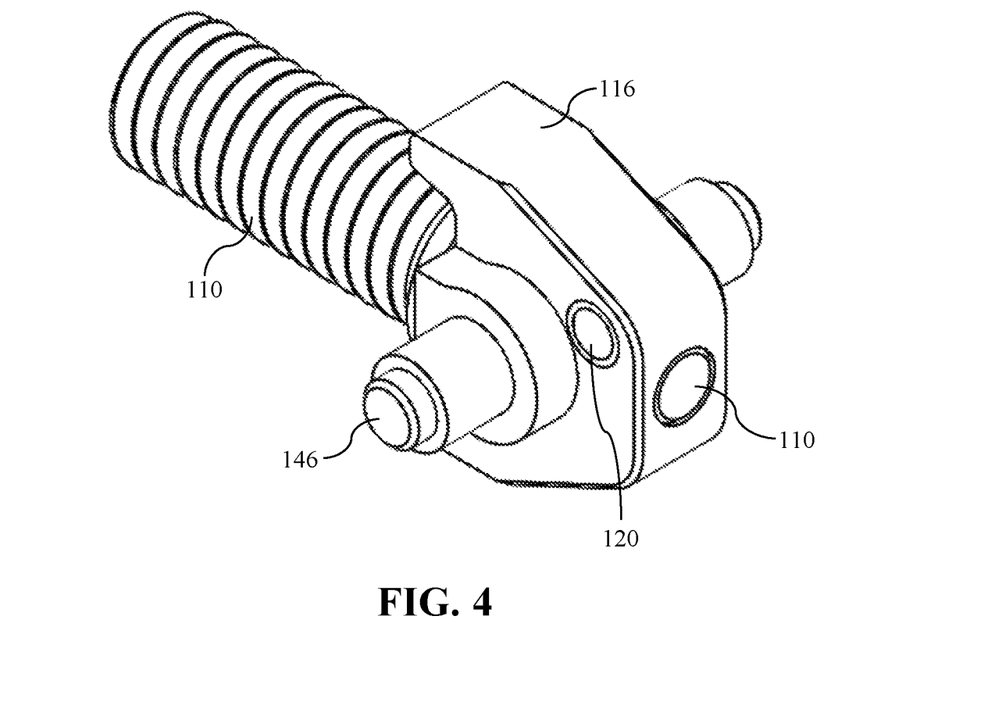
FIG. 4 is a perspective view of a screw, a distal block, and a pin, according to an embodiment.
Figure 5:
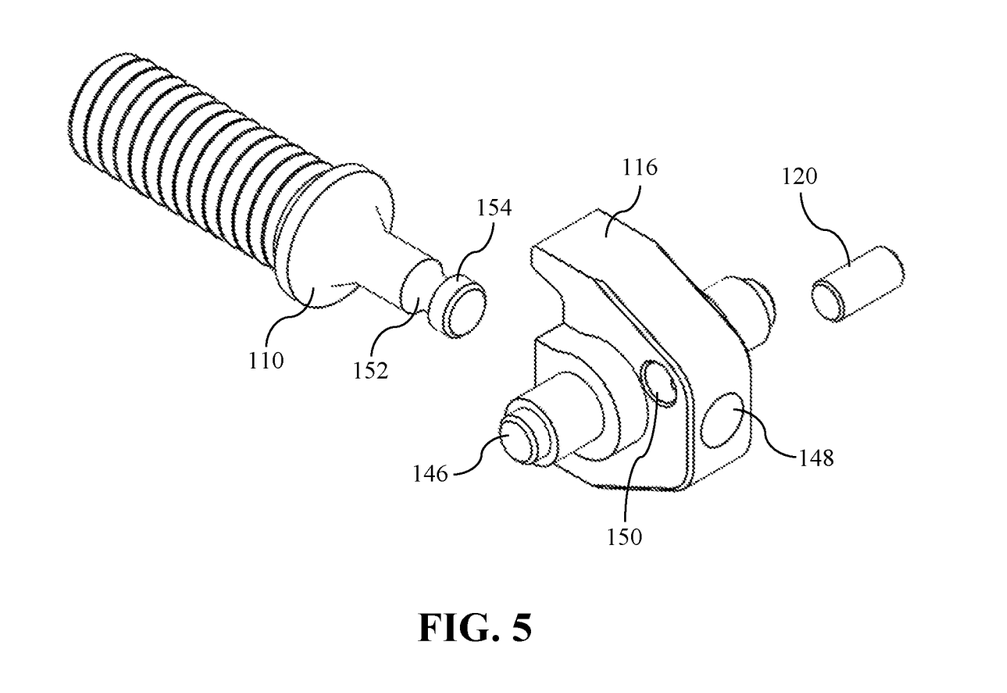
FIG. 5 is an exploded view of the screw, the distal block, and the pin according to the embodiment of FIG. 4.

Referring now to FIGS. 4-5, screw 110, distal block 116, and block pin 120 are shown. Distal block 116 includes block protrusions 146, internal passage 148, and pin channel 150. Internal passage 148 is configured to provide a passage for a portion of screw 110, as shown in FIG. 4. In some embodiments, the portion of screw 110 that passes through internal passage 148 is a shank (i.e., unthreaded), or else the internal passage 148 itself is unthreaded, or both, such that there is not co-rotation between distal block 116 and screw 110. In embodiments, screw 110 comprises screw groove 152 and nob 154. Screw 110 passes through internal passage 148 and is locked into place by block pin 120 sliding along screw groove 152 such that distal block 116 and screw 110 are fixed relative to one another in the proximal/distal directions. In embodiments, the portion of screw that is inserted into the distal block 116 may have a different width (e.g., narrower in the depicted embodiment) than the threaded portion of the screw to prevent the threaded portion from being advanced through the block.

Figure 6:
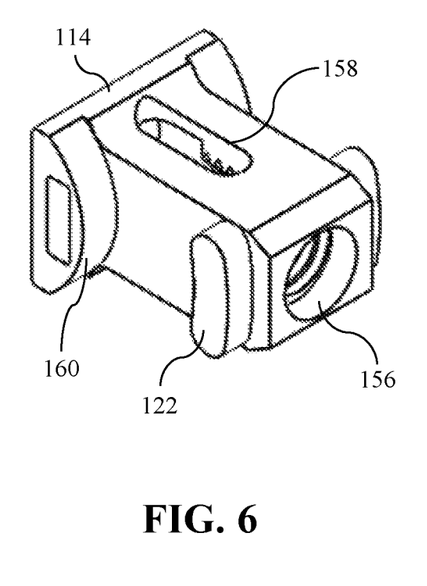
FIG. 6 is a perspective view of a proximal block, according to an embodiment.

FIG. 6 is a perspective view of proximal block 114. Proximal block 114 includes ridges 122, internal threads 156, aperture 158, and back stop 160. Internal threads 156 can be configured to interact with an adjacent component, such as screw 110 as shown in FIGS. 2A-2B. Proximal block 114 is connected to first base plate 102 and second base plate 104 via ridges 122 and tracks 124. As shown in FIG. 2B, ridges 122 can be aligned with tracks 124 within the base plates 102, 104 to allow a strong interface while allowing the base plates 102, 104 to rotate relative to the blocks 114, 116. In embodiments, back stop 160 comprises an arc to provide support against base plates 102, 104. During height expansion of base plates 102, 104, base plates 102, 104 are supported by the back stop 160 to prevent collapse during loading. Additionally, base plates 102, 104 can have rear or proximal surfaces having a concave curvature that generally matches a convex curvature of back stops 160 such that plates articulate with the arc along the back stop 160 at a very tight tolerance. Movement of base plates 102, 104 occurs along the arc.

Ridges 122 and tracks 124 guide the expansion of the base plates and provide stronger stability during torsion and shear than conventional alternatives incorporating pins or rods and passages. Although depicted as having a single ridge and corresponding track on each side, in some embodiments multiple or wider ridges and tracks can be employed. In embodiments, ridges 122 and tracks 124 comprise a curvature similar to that of the arc of back stop 160 such that ridges 122 provide further stability during articulation of base plates 102, 104. Further, ridges 122 and tracks 124 provide for expansion of base plates 102, 104 at the proximal end of the device since base plates 102, 104 do not need to be fixed with pins or rods. In devices that incorporate pins to connect base plates to a block, the pins take up room in the block such that the pins limit how wide a hole can be made in the block. The size of the hole can be crucial for a enabling a large screw or for insertion of bone fusion material. Incorporating attachment means of base plates 102, 104 to the outside of proximal block 114 enables aperture 158 to be larger in turn allowing for a larger screw or insertion of bone fusion material to be used, such as during a bone graft. Aperture 158 on a top surface of proximal block 114 further provides easier access for bone grafts. The bottom surface of proximal block 114, not visible in the perspective views herein, comprises an aperture substantially similar to aperture 158.

With continued reference to FIG. 6, rotation of screw 110 within internal threads 156 can cause screw 110 to advance in either the proximal or distal direction, which causes a corresponding movement of the distal block 116 in the same direction. As can be seen in FIG. 5, screw 110 can define a first diameter at proximal block 114 that is greater than a second diameter at distal block 116, such as the diameter of nob 154. The diameter of screw at the interface with proximal block 114 can be the same or greater than that at distal block 116 to prevent the screw from advancing distally through distal block 116. In embodiments, a ring, similar to ring 112, can prevent the screw 110 from being pulled proximally through proximal block 114.

In operation, first arms 106 and second arms 108 are rotatable and are connected to first base plate 102 and second base plate 104, respectively. Because the structural connection between first base plate 102 and screw 110 is substantially similar to the structural connection between second base plate 104 and screw 110, only the former will be described herein in detail.

First base plate 102 is mechanically coupled via base plate pins 118 to first arm 106. First arm 106 and second arm 108 are also mechanically coupled to screw 110 through distal block 116 via protrusions 146. In embodiments, a single large pin can be inserted through a channel within distal block 116 to function similarly to protrusions 146. In all, this connection permits for first base plate 102 to be indirectly connected to the screw 110 while still permitting relative rotation between them. Together with rings 112, proximal block 114, distal block 116, and base plate pins 118, a mechanical interconnection is formed between each of the base plates 102 and 104 that can be adjusted by an external tool (not shown). Ridges 122 and tracks 124 provide a pivot point that results in a specific relationship between the amount of extension of the device 100 and a relative angle between the first base plate 102 and the second base plate 104.

An external tool (not shown) can be used to turn screw 110, via a head (not shown). Because proximal block 114 is internally threaded (as shown in more detail with respect to FIG. 6), rotation of screw 110 causes relative movement of the screw 110 with respect to proximal block 114. By contrast, distal block 116 is not internally threaded. Rather, distal block 116 and screw 110 are connected such that movement of screw 110 in either the proximal or distal directions (i.e., the direction in which screw 110 moves relative to proximal block 114 when rotated) causes a corresponding movement of the distal block 116. This can be accomplished as shown, for example, in FIG. 1C, where distal block 116 is pushed and/or pulled by screw 110, and the interconnection is made by block pin 120 within groove 152. In alternative embodiments, various other interconnections between the screw and block can be made, which will result in co-movement in the proximal or distal direction without co-rotation. As proximal block 114 is moved by screw 110, it forces movement of first arms 106 and second arms 108.

As screw 110 is rotated, due to the internal threading of distal block 116, the distance between the proximal block 114 and distal block 116 changes. As the distance between proximal block 114 and distal block 116 increases, the arms 106 and 108 are caused to rotate. First arms 106 and second arms 108 rotate as the device 100 is converted from a collapsed configuration, such as that shown in FIGS. 1A-1C, to an expanded configuration, such as that shown with respect to FIGS. 2A-2B. This rotation results in increased distance between the first base plate 102 and the second base plate 104, as well as increased lordosis. As described with respect to other embodiments below, rotating screw 110 to change the distance between first base plate 102 and second base plate 104, as well as changing the amount of lordosis, can be useful to provide intervertebral support.

The embodiment shown in FIGS. 1A-1C and 2A-2B provides such intervertebral spacing, support, and lordosis with a relatively straightforward mechanical structure. The device 100 can be implanted in a compact configuration, then expanded to the appropriate size and angle by rotating screw 110, causing the changes in angle and spacing previously described, as desired.

The coupling of first arms 106 and second arms 108 to distal block 116 by protrusions 146 rather than using separate pins or other attachment means makes device 100 easier to manufacture due to the relatively large size and less parts, such as pins. Further, the use of protrusions 146 or a single large pin provides more stability than smaller pins, enabling device 100 to withstand greater loads. Protrusions 146 at a common point enables first arms 106 and second arms 108 to turn (swing) by a greater angle.

In some embodiments, when device 100 is implanted and in the process of being expanded, as blocks 114, 116 come closer together blocks 114, 116 compress a bone graft or bone fusion material that can be inserted inside device to force the material out of the internal chamber of device and into the adjacent vertebral base plates 102, 104. This will enhance bone integration into the base plates 102, 104. Some bone material will remain within the cage, which will integrate and fuse the center of the cage to the base plates 102, 104. In certain embodiments, the bone material can be injected into device 100 through one of apertures 156 in proximal block 114 of device 100. This could be done with an inserter device or separate extended syringe. In some embodiments, the base plates 102, 104 of device 100 can be coated to enhance bone integration.

Although the various devices described herein are described as being brought from a compressed configuration to an expanded configuration by rotation of a threaded member, the devices can be distracted by any other type of actuation member. In some embodiments, mechanisms other than threaded members can be used to distract the device. Such mechanisms include, for example, a pop-rivet mechanism, a sardine key and ribbon, a tourniquet and wire, a saw blade/ratchet, a zip-tie-like mechanism, piezo-electric inch worm motors and shape changing materials such as a shape member alloy or a conducting polymer actuator. These alternative locking mechanisms could be designed to make the device behave as if it were locked with a threaded member, preventing the device from being compressed as well as extended, or these mechanisms could afford the device the capability to ratchet upwards post implantation if such action would benefit the patient or provide additional therapy.

In embodiments, an expandable intervertebral cage device is adapted to be implanted into an intervertebral disc space in a patient's body. The device includes a first base plate having a first outer bearing surface configured to interface with a first vertebra of the intervertebral disc space, a second base plate having a second outer bearing surface configured to interface with a second vertebra of the intervertebral disc space, a proximal block comprising internal threading and an external ridge on each of a first side of the device and a second side of the device, the external ridges configured to move along corresponding tracks within the first base plate and the second base plate, a distal block comprising an internal passage, and two arm assemblies, wherein one arm assembly is on each of the first side of the device and the second side of the device. Each arm assembly includes a first arm mechanically coupled to the first base plate and the distal block and a second arm mechanically coupled to the second base plate and the distal block. The device further includes a screw extending between the internal threading of the proximal block and the internal passage of the distal block, such that rotation of the screw relative to the proximal block causes a change in distance between the distal block and the proximal block, and a corresponding change in the spacing and lordosis of the device due to an expansion or contraction of the arm assemblies as the external ridges on the proximal block are guided through the corresponding tracks within the first base plate and the second base plate.

In some embodiments, the change in distance between the distal block and the proximal block causes the first base plate and the second base plate to move along an external arced surface of the proximal block on each of the first side and the second side.

In some embodiments, the device comprises only two arm assemblies.

In some embodiments, both the first arm and the second arm of each arm assembly are mechanically coupled to a common point on the distal block.

In some embodiments, the proximal block has an opening defined therein sized and configured in enable insertion of a bone growth material into an open area within the device.

In some embodiments, the top base plate and the bottom base plate each have an opening defined therein configured to allow bone growth into an open space defined by the device.

In some embodiments, the screw is threadedly coupled to the internal threading of the proximal block, and the distal block includes a non-threaded rotational coupling to which the screw is non-threadedly rotationally coupled.

In some embodiments, the screw includes a first portion having a first diameter and a second portion having a second diameter.

In some embodiments, rotation of the screw relative to the proximal block further causes the arm assemblies to expand an angle of the first base plate and the second base plate relative to each other.

In some embodiments, the change in distance between the distal block and the proximal block causes a distance between a proximal end of the first base plate and a proximal end of the second base plate to vary.

In embodiments, an expandable intervertebral cage device adapted to be implanted into an intervertebral disc space in a patient's body includes a first base plate having a first outer bearing surface configured to interface with a first vertebra of the intervertebral disc space, a second base plate having a second outer bearing surface configured to interface with a second vertebra of the intervertebral disc space, a proximal block comprising internal threading and an external arced surface on each of a first side of the device and a second side of the device, a distal block comprising an internal passage and one arm assembly on each of the first side of the device and the second side of the device. Each arm assembly can include a first arm mechanically coupled to the first base plate and the distal bloc and a second arm mechanically coupled to the second base plate and the distal block. A screw can extend between the internal threading of the proximal block and the internal passage of the distal block such that rotation of the screw relative to the proximal block causes a change in distance between the distal block and the proximal block and a corresponding movement of the first base plate and the second base plate along the external arced surfaces of the proximal block.

In some embodiments, a distance between a proximal end of the first base plate and a proximal end of the second base plate varies as the first base plate and the second base plate move along the external arced surfaces.

In some embodiments, the device comprises only two arm assemblies.

In some embodiments, both the first arm and the second arm of each arm assembly are mechanically coupled to a common point on the distal block.

In some embodiments, the proximal block further comprises an external ridge on each of the first side of the device and the second side of the device, the external ridges configured to move along corresponding tracks within the first base plate and the second base plate as the first base plate and the second base plate move along the external arced surfaces.

In some embodiments, the proximal block has an opening defined therein sized and configured in enable insertion of a bone growth material into an open area within the device.

In some embodiments, the top base plate and the bottom base plate each have an opening defined therein configured to allow bone growth into an open space defined by the device.

Various embodiments of systems, devices, and methods have been described herein. These embodiments are given only by way of example and are not intended to limit the scope of the disclosure. It should be appreciated, moreover, that the various features of the embodiments that have been described may be combined in various ways to produce numerous additional embodiments. Moreover, while various materials, dimensions, shapes, configurations, and locations, etc. have been described for use with disclosed embodiments, others besides those disclosed may be utilized without exceeding the scope of the disclosure.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An expandable intervertebral cage device adapted to be implanted into an intervertebral disc space in a patient's body, comprising:
   a first base plate having a first outer bearing surface configured to interface with a first vertebra of the intervertebral disc space and a first elongate track;
   a second base plate having a second outer bearing surface configured to interface with a second vertebra of the intervertebral disc space and a second elongate track;
   a proximal block comprising internal threading and an external ridge on each of a first side of the device and a second side of the device, the external ridges configured to be inserted into the first elongate track and the second elongate track, respectively, and each including a concave surface and a convex surface;
   a distal block comprising an internal passage;
   two arm assemblies, wherein one arm assembly is on each of the first side of the device and the second side of the device and wherein each arm assembly comprises:
      a first arm pivotally coupled to the first base plate and the distal block; and
      a second arm pivotally coupled to the second base plate and the distal block; and
   a screw extending between internal threading of the proximal block and the internal passage of the distal block, such that rotation of the screw relative to the proximal block causes a change in distance between the distal block and the proximal block, and a corresponding change in the spacing and lordosis of the device as the external ridges on the proximal block guide the corresponding tracks within the first base plate and the second base plate in a direction of movement of the first base plate and the second base plate.

2. The device of claim 1, wherein the change in distance between the distal block and the proximal block causes the first base plate and the second base plate to move along an external arced surface of the proximal block on each of the first side and the second side.

3. The device of claim 1, comprising only two arm assemblies.

4. The device of claim 1, wherein both the first arm and the second arm of each arm assembly are mechanically coupled to a common point on the respective side of the distal block.

5. The device of claim 1, wherein the proximal block has an opening defined therein sized and configured to enable insertion of a bone growth material into an open area within the device.

6. The device of claim 1, wherein the fir t base plate and the second base plate each have an opening defined therein configured to allow bone growth into an open space defined by the device.

7. The device of claim 1, wherein the screw is threadedly coupled to the internal threading of the proximal block, and the distal block includes a non-threaded rotational coupling to which the screw is non-threadedly rotationally coupled.

8. The device of claim 1, wherein the screw includes a first portion having a first diameter and a second portion having a second diameter.

9. The device of claim 1, wherein rotation of the screw relative to the proximal block further causes the arm assemblies to expand an angle of the first base plate and the second base plate relative to each other.

10. The device of claim 1, wherein the change in distance between the distal block and the proximal block causes a distance between a proximal end of the first base plate and a proximal end of the second base plate to vary.

11. The device of claim 1, wherein the external ridges and the first and second elongate tracks are curved.

12. An expandable intervertebral cage device adapted to be implanted into an intervertebral disc space in a patient's body, comprising:
   a first base plate having a first outer bearing surface configured to interface with a first vertebra of the intervertebral disc space;
   a second base plate having a second outer bearing surface configured to interface with a second vertebra of the intervertebral disc space;
   a proximal block comprising internal threading and an external convex arced surface on each of a first side of the device and a second side of the device, wherein the proximal block further comprises an external ridge on each of the first side of the device and the second side of the device each including a concave surface and a convex surface;
   a distal block comprising an internal passage;
   two arm assemblies, wherein one arm assembly is on each of the first side of the device and the second side of the device and wherein each arm assembly comprises:
      a first arm pivotally coupled to the first base plate and the distal block; and
      a second arm pivotally coupled to the second base plate and the distal block; and
   a screw extending between the internal threading of the proximal block and the internal passage of the distal block, such that rotation of the screw relative to the proximal block causes a change in distance between the distal block and the proximal block, and a corresponding movement of the first base plate and the second base plate along the external convex arced surfaces of the proximal block.

13. The device of claim 12, wherein a distance between a proximal end of the first base plate and a proximal end of the second base plate varies as the first base plate and the second base plate move along the external arced surfaces.

14. The device of claim 12, comprising only two arm assemblies.

15. The device of claim 12, wherein both the first arm and the second arm of each arm assembly are mechanically coupled to a common point on the respective side of the distal block.

16. The device of claim 12, wherein corresponding tracks within the first base plate and the second base plate are configured to move along the external ridges as the first base plate and the second base plate move along the external arced surfaces.

17. The device of claim 16, wherein the external ridges and the corresponding tracks are curved.

18. The device of claim 17, wherein a curvature of the external ridges and the corresponding tracks matches a curvature of the external arced surfaces.

19. The device of claim 12, wherein the proximal block has an opening defined therein sized and configured to enable insertion of a bone growth material into an open area within the device.

20. The device of claim 12, wherein the first base plate and the second base plate each have an opening defined therein configured to allow bone growth into an open space defined by the device.

* * * * *